(12) United States Patent
Nishiuchi

(10) Patent No.: US 8,157,749 B2
(45) Date of Patent: Apr. 17, 2012

(54) BLOOD COMPONENT MEASUREMENT DEVICE AND TIP FOR BLOOD MEASUREMENT

(75) Inventor: Daisuke Nishiuchi, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1035 days.

(21) Appl. No.: 11/920,414

(22) PCT Filed: May 16, 2006

(86) PCT No.: PCT/JP2006/309756
§ 371 (c)(1), (2), (4) Date: Nov. 15, 2007

(87) PCT Pub. No.: WO2006/123665
PCT Pub. Date: Nov. 23, 2006

(65) Prior Publication Data
US 2009/0105613 A1    Apr. 23, 2009

(30) Foreign Application Priority Data
May 16, 2005 (JP) .................... 2005-142262

(51) Int. Cl.
*A61B 5/00* (2006.01)
*A61B 17/32* (2006.01)
*A61B 17/14* (2006.01)
*B65D 81/00* (2006.01)

(52) U.S. Cl. ......... 600/584; 600/583; 600/573; 606/181

(58) Field of Classification Search .................. 600/583, 600/584, 573, 576; 606/181–183
See application file for complete search history.

(56) References Cited

U.S. PATENT DOCUMENTS

| 6,866,675 | B2 | 3/2005 | Perez et al. |
| 7,749,174 | B2* | 7/2010 | Alden et al. ............... 600/583 |
| 2002/0169393 | A1* | 11/2002 | Cunningham et al. ....... 600/573 |
| 2002/0188223 | A1 | 12/2002 | Perez et al. |

(Continued)

FOREIGN PATENT DOCUMENTS

| JP | 2004-033438 A | 2/2004 |
| JP | 2004-033439 A | 2/2004 |
| JP | 2005-501591 A | 1/2005 |
| JP | 2006-014789 A | 1/2006 |
| WO | WO 01/41643 A1 | 6/2001 |
| WO | WO 03/020134 A2 | 3/2003 |

OTHER PUBLICATIONS

International Search Report for PCT/JP2006/309756 dated Jun. 6, 2006.

*Primary Examiner* — Max Hindenburg
*Assistant Examiner* — H. Q. Nguyen
(74) *Attorney, Agent, or Firm* — Buchanan Ingersoll & Rooney PC

(57) ABSTRACT

A blood component measurement device (10) has a puncturing unit (18) provided inside a housing (12) and having a puncture needle (16); a button unit (20) for advancing and retreating the puncture needle (16); a contact mechanism (68) coming into contact with the skin of a person to be measured; and a holder (14) for displaceably holding the puncturing unit (18). The blood component measurement device (10) also has an introduction section (94) at the substantially center of a contact member (70). After the skin is punctured by the puncture needle (16) provided at the substantially center of the mechanism (68), the introduction section (94) introduces blood to testing paper (100) when the contact member (70) of the contact mechanism (68) is displaced in a sliding manner along a guide member (72).

12 Claims, 11 Drawing Sheets

U.S. PATENT DOCUMENTS

| | | | |
|---|---|---|---|
| 2002/0188224 A1* | 12/2002 | Roe et al. | 600/584 |
| 2002/0198444 A1 | 12/2002 | Uchigaki et al. | |
| 2003/0212345 A1* | 11/2003 | McAllister et al. | 600/584 |
| 2004/0116829 A1* | 6/2004 | Raney et al. | 600/573 |
| 2004/0215224 A1* | 10/2004 | Sakata et al. | 606/181 |
| 2004/0236251 A1* | 11/2004 | Roe et al. | 600/583 |
| 2005/0033341 A1* | 2/2005 | Vreeke et al. | 606/181 |
| 2005/0234368 A1* | 10/2005 | Wong et al. | 600/583 |
| 2006/0047220 A1 | 3/2006 | Sakata et al. | |
| 2006/0229532 A1* | 10/2006 | Wong et al. | 600/583 |

* cited by examiner

BLOOD COMPONENT MEASUREMENT DEVICE AND TIP FOR BLOOD MEASUREMENT

TECHNICAL FIELD

The present invention relates to a blood component measurement device for measuring a component, such as glucose, of blood. More particularly, the invention relates to a tip for blood measurement which has a puncture needle capable of being advanced and retreated in the axial direction thereof, and to a blood component measurement device having the tip for blood measurement.

BACKGROUND ART

In recent years, diabetics are recommended to make daily self-control by measuring the variations in blood sugar level by themselves. For the measurement of blood sugar level, a blood component measurement device has been put into practical use, in which a test paper impregnated with a reagent capable of coloration according to the quantity of glucose in blood is mounted, blood is supplied to the test paper to effect coloration, and the degree of coloration is optically measured to thereby determine and display the blood sugar level. In addition, a blood component measurement device using an electrochemical sensor has also been put to practical use.

When a patient samples his own blood, a puncture needle capable of being advanced and retreated in the axial direction thereof is instantaneously projected by applying a repelling force of an elastic body to the puncture needle, whereby the patient's skin is punctured by the puncture needle and a minute amount of blood is let bleed. Such a puncture needle tip is integrally provided with a measurement member such as a test paper and mounted to a blood component measurement device, and measurement is conducted by use of the device, whereby a puncturing step and a measuring step are performed automatically and continuously.

For example, such a blood component measurement device as above-mentioned is disclosed in Japanese Patent Laid-open No. 2004-33438 or Japanese Patent Laid-open No. 2004-33439, in which a puncture member having a needle capable of being advanced and retreated along the axial direction is provided at the substantially center of a casing, and a tip-formed sensor is disposed at such a position as to approach the needle when the puncture member is displaced toward the human body side. The sensor is provided to be spaced by a predetermined distance in a radial direction of a circle, with the needle as a center of the circle, and, when the needle is let puncture the skin of the human body, the blood bleeding from the skin flows toward the sensor side, to be led to the test paper.

In addition, another blood component measurement device is disclosed in U.S. Pat. No. 6,866,675, in which a puncture needle is passed through the inside of a blood sampling capillary tube, and a mouth of the capillary tube is disposed directly above a punctured part of a skin so that blood is sampled from the punctured part and served to measurement.

Meanwhile, according to the related art as above-mentioned, the needle for puncturing the skin and causing blood to flow out and a blood introduction port for leading the blood having flowed out to the measurement unit are spaced by a predetermined distance from each other. More specifically, the needle of the puncture member is disposed on the center axis of the blood component measurement device, and the blood introduction port is spaced by a predetermined distance from the axis. As a result, the punctured part of the skin where blood is let flow out by the needle and the blood introduction port for guiding the blood are spaced from each other, so that a large amount of blood must bleed until the blood comes into contact with the blood introduction section, in the process of guiding the blood to the measurement unit.

Besides, according to the related art as above-mentioned, the configuration wherein the puncture needle is disposed in a capillary tube causes difficulties in design, layout or the like of the measurement unit for measuring a component of blood, and makes it difficult to achieve the desired measurement by use of a measurement device simple in configuration.

DISCLOSURE OF INVENTION

It is a principal object to provide a blood component measurement device and a tip for blood measurement in which blood let flow out by puncturing is efficiently introduced to a measurement unit, whereby component measurement can be achieved while using a minute amount of blood.

In order to attain the above object, according to the present invention, there is provided a blood component measurement device having a tip for blood measurement including a puncture needle capable of being advanced and retreated in the axial direction thereof, wherein the blood component measurement device also has: a contact section which has a cavity permitting the puncture needle to pass therethrough and which comes into contact with a skin, and a measurement unit for measuring a component of blood sampled; and a blood introduction section spaced from the puncture needle in a direction substantially orthogonal to the axis of the puncture needle and communicating with the measurement unit, and after the skin is punctured by the puncture needle, the blood introduction section is displaced in a direction substantially orthogonal to the axis of the puncture needle toward the axis of the puncture needle and is displaced in the axial direction of the puncture needle toward the skin.

According to the present invention, the contact section is brought into contact with the skin, and the puncture needle is passed through the cavity in the contact part to puncture the skin, whereby blood is let flow out from the skin. After the puncturing is finished, the blood introduction section is displaced in a direction substantially orthogonal to the axis of the puncture needle, whereby it is displaced toward the skin where the blood is flowing out.

Therefore, by displacing the blood introduction section so as to approach the blood, the blood can be efficiently introduced through the blood introduction section to the measurement unit. Accordingly, the desired measurement in the blood component measurement device can be achieved with a minuter amount of blood.

In addition, preferably, the blood component measurement device further has a guide section for holding the contact section displaceably in a direction at a predetermined angle to the axis of the puncture needle, and the blood introduction section is displaced under a guiding action of the guide section. This ensures that after the puncturing step by the puncture needle is finished, the blood introduction section can be brought closer to blood by displacing the blood introduction section in a direction at a predetermined angle toward the axis of the puncture needle under the guiding action of the guide section. Therefore, the blood having flowed out can be efficiently introduced to the measurement unit through the blood introduction section.

Further, when the tip for blood measurement is provided with the contact section, the contact part can be detachably attached to the blood component measurement device and, therefore, it can be replaced readily.

Furthermore, when the tip for blood measurement is provided with the blood introduction section, the blood introduction section can be detachably attached to the blood component measurement device and, therefore, the measurement unit can be readily replaced after measurement of a blood component is completed.

Furthermore, when the tip for blood measurement is provided with the measurement unit, the measurement unit can be detachably attached to the blood component measurement device and, therefore, the measurement unit can be readily replaced after measurement of a blood component is completed.

Besides, preferably, the blood component measurement device has a stopper for restricting the displacement of the contact section, and the condition where the displacement of the contact section is restricted by the stopper is canceled after puncture by the puncture needle is conducted. This ensures that, at the time of puncturing a skin by the puncture needle, the puncture needle is securely locked in the state of being located at the substantially center of the contact section by the stopper. On the other hand, after the puncture by the puncture needle is finished, the restricted condition by the stopper can be canceled to thereby realize a condition where the blood introduction section is located at the substantially center of the contact section.

Further, preferably, the contact section is provided with a first slant surface opposed to the guide section and inclined at a predetermined angle, the guide section is provided with a second slant surface making contact with the first slant surface and being at substantially the same angle as the first slant surface, and the contact section is displaced along the second slant surface through the first slant surface. This ensures that the contact section can be displaced in a direction at a predetermined angle relative to the guide section, so that in the case where blood is let flow out from the punctured portion in a convex shape in the manner of swelling from the skin, the contact section can be brought closer to the blood introduction section gradually from an oblique direction. As a result, in the process of displacement of the contact section, the blood can be prevented from making contact with the surroundings of the blood introduction section; therefore, diffusion of the blood due to the contact of the blood with the surroundings of the blood introduction section can be prohibited, as contrasted to the case where the blood introduction section is brought closer to the blood from a horizontal direction.

Besides, preferably, the blood component measurement device has a housing, a button unit for canceling the condition where the advancing and retreating of the puncture needle are restricted is displaceably disposed inside said housing, and the puncture needle is pushed toward the contact section side by operating the button unit to cancel the condition where the displacement of the puncture needle is restricted. This ensures that the puncture needle can be displaced relative to the housing toward the contact section side by the button unit and, therefore, the operation of puncturing by the puncture needle can be easily carried out.

Furthermore, according to the present invention, there is provided a structure including: a puncture needle capable of being advanced and retreated in the axial direction thereof; a contact section which has a cavity permitting the puncture needle to pass therethrough and which comes into contact with a skin, and a measurement unit for measuring a component of blood sampled; a blood introduction section spaced from the puncture needle in a direction substantially orthogonal to the axis of the puncture needle and communicating with the measurement unit; and a guide section for holding the contact section displaceably in a direction at a predetermined angle relative to the axis of the puncture needle.

According to the present invention, the contact section in the tip for blood measurement is brought into contact with a skin, and the puncture needle is passed through the cavity in the contact section to puncture the skin, whereby blood is let flow out from the skin. After the puncturing step is finished, the blood introduction section is displaced in a direction at a predetermined angle under the guiding action of the guide section, and the blood introduction section displaced from the puncture needle in a direction substantially orthogonal to the puncture needle is brought closer to the axis of the contact section, whereby the blood introduction section can be put into a position close to the blood. As a result, the blood can be efficiently introduced to the measurement unit through the blood introduction section, and the measurement by the blood component measurement device can be performed while using a minuter amount of blood.

In addition, preferably, the contact section is provided with a first slant surface opposed to the guide section and inclined at a predetermined angle, the guide section is provided with a second slant surface making contact with the first slant surface and being at substantially the same angle as the first slant surface, and the contact section is displaced along the second slant surface through the first slant surface. This ensures that the contact section can be displaced in a direction at a predetermined angle relative to the guide section; therefore, in the case where blood is left flow out into a convex shape in the manner of swelling from the skin at the punctured portion, the contact section can be brought closer to the blood introduction section gradually from an oblique direction. As a result, in the process of displacement of the contact section, the blood can be prevented from making contact with the surroundings of the blood introduction section. Accordingly, diffusion of the blood due to contact of the blood with the surroundings of the blood introduction section can be prohibited, as contrasted to the case where the blood introduction section is brought closer to the blood from a horizontal direction.

Further, there is provided a structure including: a mounted section to be mounted to a blood component measurement device; a contact section which has a cavity permitting the puncture needle to pass therethrough and which comes into contact with a skin; and a measurement unit for measuring a component of blood sampled, wherein the contact section is so held as to be displaceable relative to the mounted section.

According to the present invention, there is provided a configuration in which the tip for blood measurement can be detachably attached to a blood component measurement device through the mounted section, and, therefore, the tip for blood measurement can be replaced easily and speedily.

Thus, according to the present invention, the contact section is brought into contact with the surroundings of a punctured portion of a skin, the punctured portion is punctured by the puncture needle disposed at the contact section, and thereafter the blood introduction section is displaced in a direction substantially orthogonal to the axis of the puncture needle and is thereby displaced toward the skin where the blood is flowing out. This ensures that the blood introduction section can be set close to the blood let flow out by the puncture needle, the blood let flow out by the puncture needle can be efficiently introduced to the measurement unit through the blood introduction section, and the measurement by the blood component measurement device can be performed while using a minuter amount of blood.

BEST MODE FOR CARRYING OUT THE INVENTION

Figure 1:
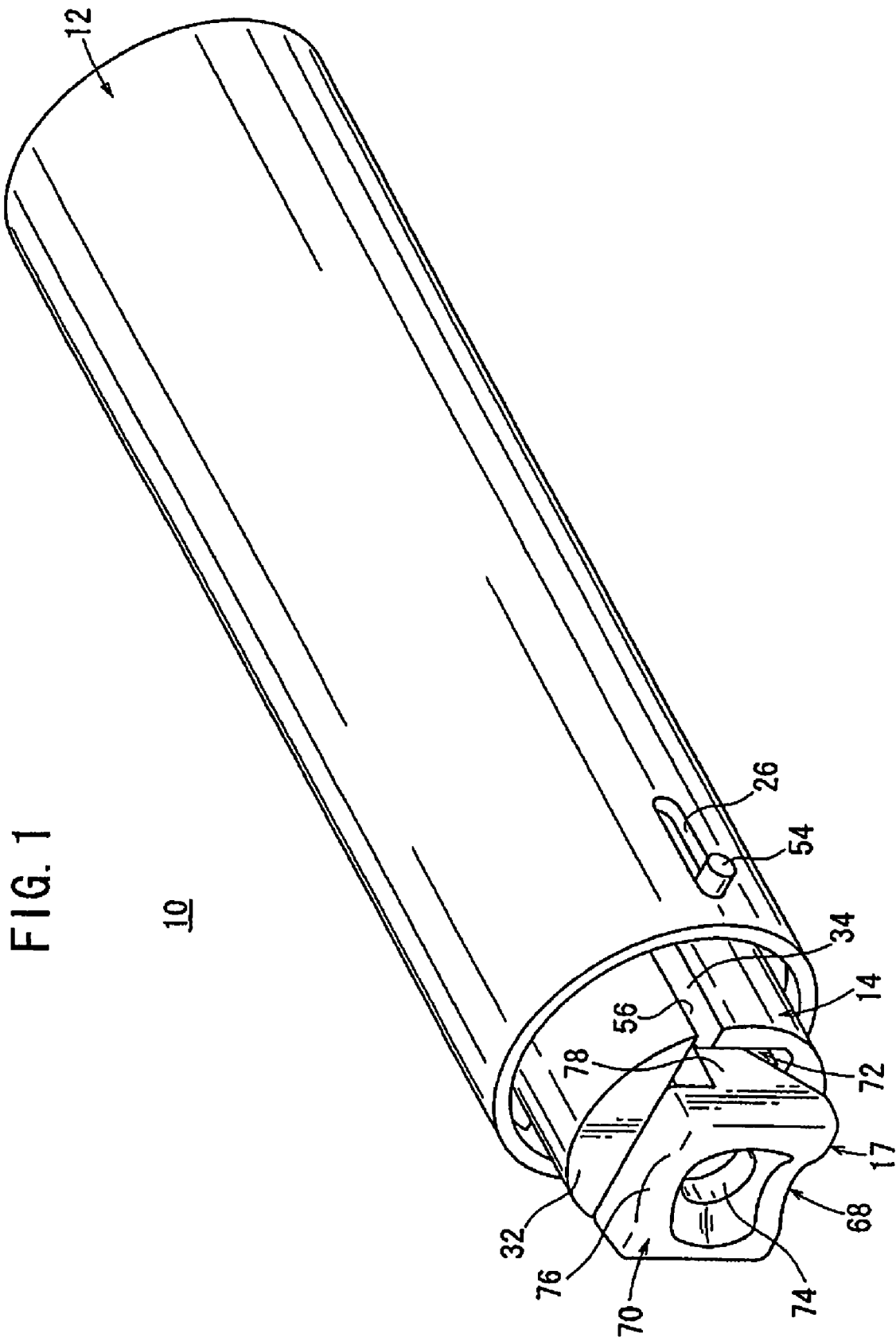
FIG. 1 is a perspective view of appearance of a blood component measurement device according to an embodiment of the present invention.

In FIG. 1, reference symbol 10 denotes a blood component measurement device according to an embodiment of the present invention. Incidentally, the blood component measurement device 10 according to this embodiment is for measuring a component, such as glucose, of blood or the amount of the component (hereinafter referred to as blood sugar level).

Figure 2:
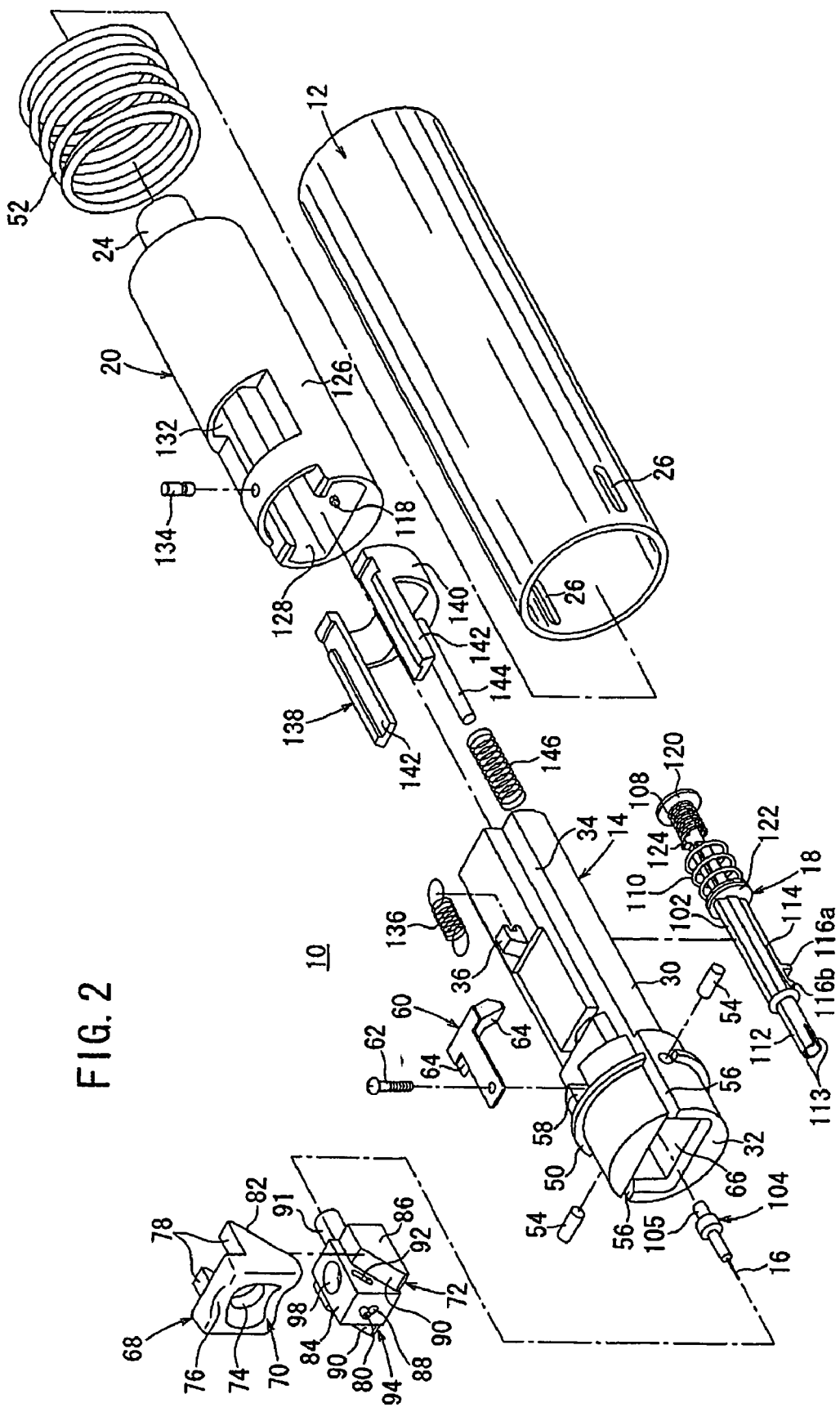
FIG. 2 is an exploded perspective view of the blood component measurement device of FIG. 1.
Figure 3:
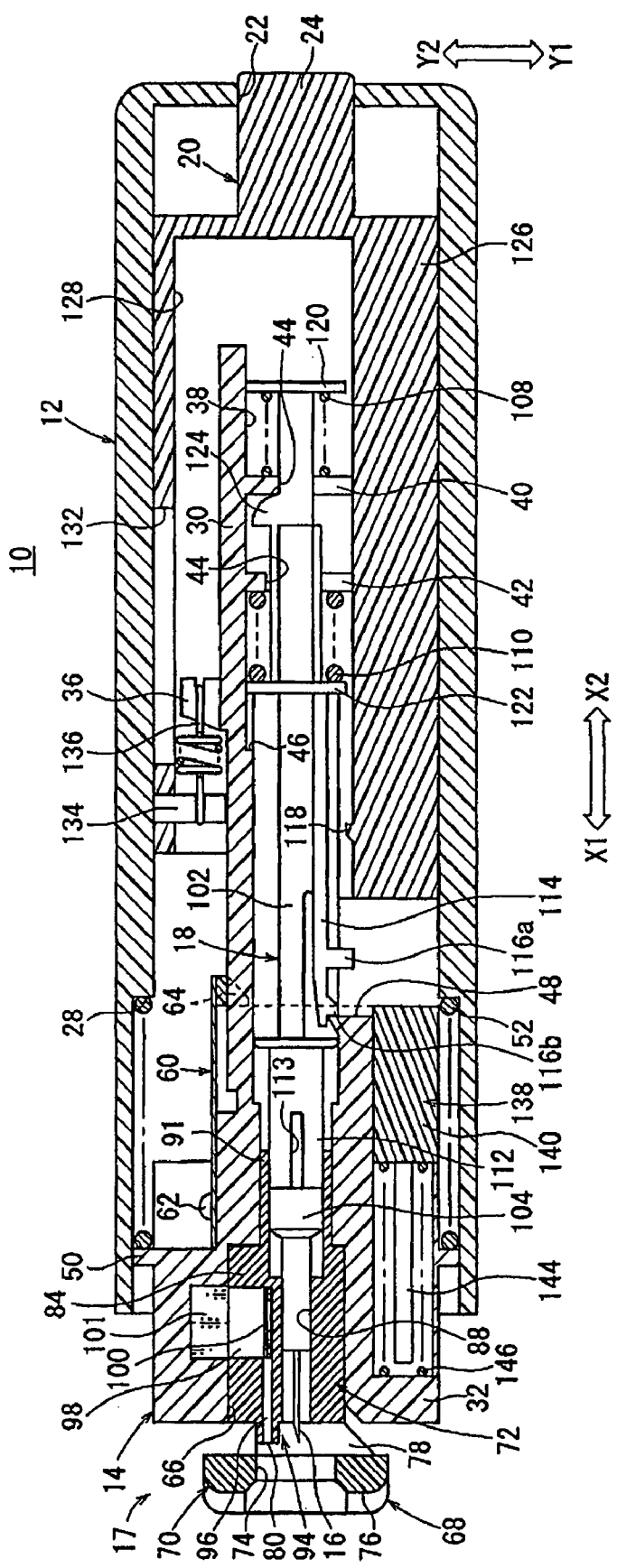
FIG. 3 is an overall longitudinal sectional view of the blood component measurement device.

As shown in FIGS. 1 to 3, the blood component measurement device 10 has a cylindrically formed housing 12, a holder 14 displaceably provided inside the housing 12, a tip for blood measurement 17 held by the holder 14 and including a puncture needle 16, a puncturing unit 18 for advancing and retreating the puncture needle 16 in the axial direction of the latter, and a button unit 20 (see FIGS. 2 and 3) for changeover between advancing and retreating of the puncture needle 16.

The housing 12 is formed in a bottomed shape opened on one end side and closed on the other end side, and a button hole 22 is formed in a substantially central part of the other end. A button section 24 is inserted in the button hole 22 when the button unit 20 is disposed inside the housing 12.

In addition, on one end side of the housing 12, a pair of slots 26 which each have a predetermined length along the axial direction and which are opposed to each other are formed in an outer peripheral surface of the housing 12.

Further, the inner peripheral surface of the housing 12 is formed to be enlarged radially outwards on one end side as compared with the other end side, and a step 28 is formed at the boundary between the inner peripheral surface on one end side and the inner peripheral surface on the other end side which surfaces are different in inside diameter.

The holder 14 has a main body section 30 having a predetermined length along the axial direction, and a hollow cylindrical section 32 formed on one end side of the main body section 30 and formed in correspondence with the inner peripheral shape of the housing 12. The holder 14 is inserted into the inside of the housing 12 from the main body section 30 side, and a puncturing unit 18 is disposed in the inside of the holder 14.

The main body section 30 has a pair of guide grooves 34 adjacent to both side surfaces along the axial direction, and a projected part 36 projected from an upper surface of the main body section 30 which surface is present between the guide grooves 34. Incidentally, each of the guide grooves 34 has its upper surface formed in a substantially flat surface shape.

In addition, the main body section 30 is provided with a first mount hole 38 opened in a substantially U-shaped sectional shape toward the lower side, i.e., in the direction of arrow Y1. The first mount hole 38 includes a first engagement wall 40 projected downwards (in the direction of arrow Y1) from an inner peripheral surface of the first mount hole 38, and a second engagement wall 42 formed on the hollow cylindrical section 32 side (the direction of arrow X1) relative to the first engagement wall 40 (see FIG. 3). The first and second engagement walls 40 and 42 are provided with groove parts 44 at substantially the centers thereof. In the groove parts 44 opened toward the lower side (in the direction of arrow Y1), a part of the puncturing unit 18 is inserted in the manner of being displaceable along the axial direction.

The first mount hole 38 is provided with a first step part 46 where the inner wall surface on the hollow cylindrical section 32 side (the direction of arrow X1) relative to the second engagement wall 42 is bulged toward the lower side, i.e., toward the puncturing unit 18 side (in the direction of arrow Y1). In addition, the first mount hole 38 is provided with a second step part 48 on the hollow cylindrical section 32 side (the direction of arrow X1) relative to the first step part 46. The second step part 48 is opposed to the first step part 46, with the puncturing unit 18 therebetween, and is bulged toward the puncturing unit 18 side (in the direction of arrow Y2). Incidentally, the second step part 48 is provided at a position on the lower side (the direction of arrow Y1) in relation to the puncturing unit 18.

The outer peripheral surface of the hollow cylindrical section 32 is provided with an annular flange part 50 projected radially outwards, and the peripheral surface of the flange part 50 makes contact with the inner peripheral surface of the housing 12 when the holder 14 is inserted in the inside of the housing 12. In other words, the flange part 50 functions as a guide when the holder 14 is displaced along the inside of the housing 12.

A coil spring 52 is interposed between the flange part 50 and the step part 28 of the housing 12, and a springy force of the coil spring 52 biases in the manner of pushing the holder 14 toward the opened one end side of the housing 12 (in the direction of arrow X1) through the hollow cylindrical section 32.

In addition, the flange part 50 of the hollow cylindrical section 32 is partly cut out, and a pair of guide pins 54 are mounted in the cut-out portions. The guide pins 54 are provided at such positions as to be substantially symmetric with each other, with the axis of the hollow cylindrical section 32 as a center, and are mounted so as to project by a predetermined length in relation to the outer peripheral surface of the hollow cylindrical section 32. When the holder 14 is inserted in the inside of the housing 12, the guide pins 54 are engaged respectively with the slots 26 in the housing 12, and the holder 14 is so held as to be displaceable along the axial direction in relation to the housing 12. In this case, the amount of displacement of the holder 14 is substantially equal to the length of the slots 26 along the axial direction.

Further, the hollow cylindrical section 32 is cut out at portions located on the extensions of the guide grooves 34 in the main body section 30, whereby a pair of cutouts 56 substantially flush with the guide grooves 34 are formed. The cutouts 56 penetrate the inside of the hollow cylindrical section 32 in the axial direction.

The hollow cylindrical section 32 is provided with a recess 58 recessed to the flange part 50 side from an end face on the main body section 30 side, at a position between the pair of cutouts 56. The recess 58 extends from the outer peripheral surface of the hollow cylindrical section 32 in a direction substantially orthogonal to the axis of the hollow cylindrical part 32, and a stopper hook 60 is mounted to the hollow cylindrical section 32 through the recess 58.

The stopper hook 60 is formed in a substantially T shape from a flexible metallic material. One end part of the stopper hook 60 is fixed to the recess 58 through a fixing screw 62, and the other end side of the stopper hook 60 extends by a predetermined length in substantially orthogonal directions, with the one end part as a center.

The other end part of the stopper hook 60 is extended to such a positions as to be opposed to the pair of guide grooves 34, and hook parts 64 are projected therefrom toward the guide groove 34 sides (in the direction of arrow Y1). The hook parts 64 are engaged with an end face of a stopper 138 (described later) disposed inside the housing 12 to restrict the displacement of the stopper 138 toward the button unit 20 side (in the direction of arrow X2) (see FIG. 5).

More specifically, the stopper hook 60 is so provided that its other end side can be tilted in such a direction as to be spaced away from the holder 14, with its one end part fixed by the fixing screw 62 as a fulcrum.

On the other hand, the hollow cylindrical section 32 is provided in a substantially central part thereof with a second mount hole 66 opened in a substantially rectangular shape, and the second mount hole 66 communicates with the first mount hole 38 formed in the main body section 30. The second mount hole 66 is larger than the first mount hole 38 in sectional shape, and the tip for blood measurement 17 including the contact mechanism 68 capable of making contact with the skin of a person to be measured is disposed inside the second mount hole 66.

The tip for blood measurement 17 includes a puncture needle 16, a hub 104 for holding the puncture needle 16, the contact mechanism 68 which holds the hub 104 displaceably along the axial direction and which can make contact with the skin of the person to be measured, and a test paper (measurement unit) 100 provided in the contact mechanism 68 and mounted in a circular recess 98 into which blood is introduced. Incidentally, the puncture needle 16 is preliminarily sterilized, and the sterilized state is maintained until use.

The hub 104 is formed in a cylindrical shape. The puncture needle 16 is mounted to one end side of the hub 104, and a reduced diameter section 105 formed on the other end side is inserted into a hub gripping section 112 (described later) of the puncturing unit 18. This results in that the hub 104 is so held as to be detachably attached to the puncturing unit 18.

Figure 11:
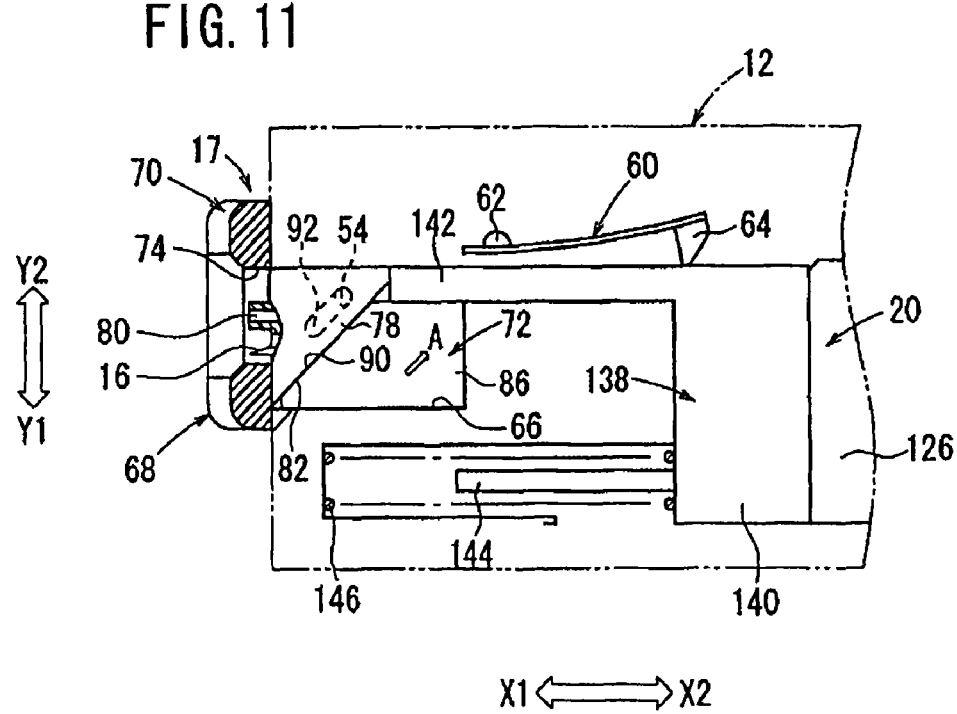
FIG. 11 is a schematic configuration view showing the positional relationships between the contact member and the guide member, in the contact mechanism of FIG. 10, and the introduction part and the puncturing unit.

The contact mechanism 68 includes a contact member (contact section) 70 coming into contact with the surroundings of a punctured portion of the skin of a person to be measured, and a guide member (guide section) 72 for holding the contact member 70 so that the contact member 70 is displaceable in an oblique direction (the direction of arrow A, in FIG. 11) inclined at a predetermined angle relative to the axis of the holder 14. The guide member 72 is mounted in the second mount hole 66 in the holder 14.

Figure 4:
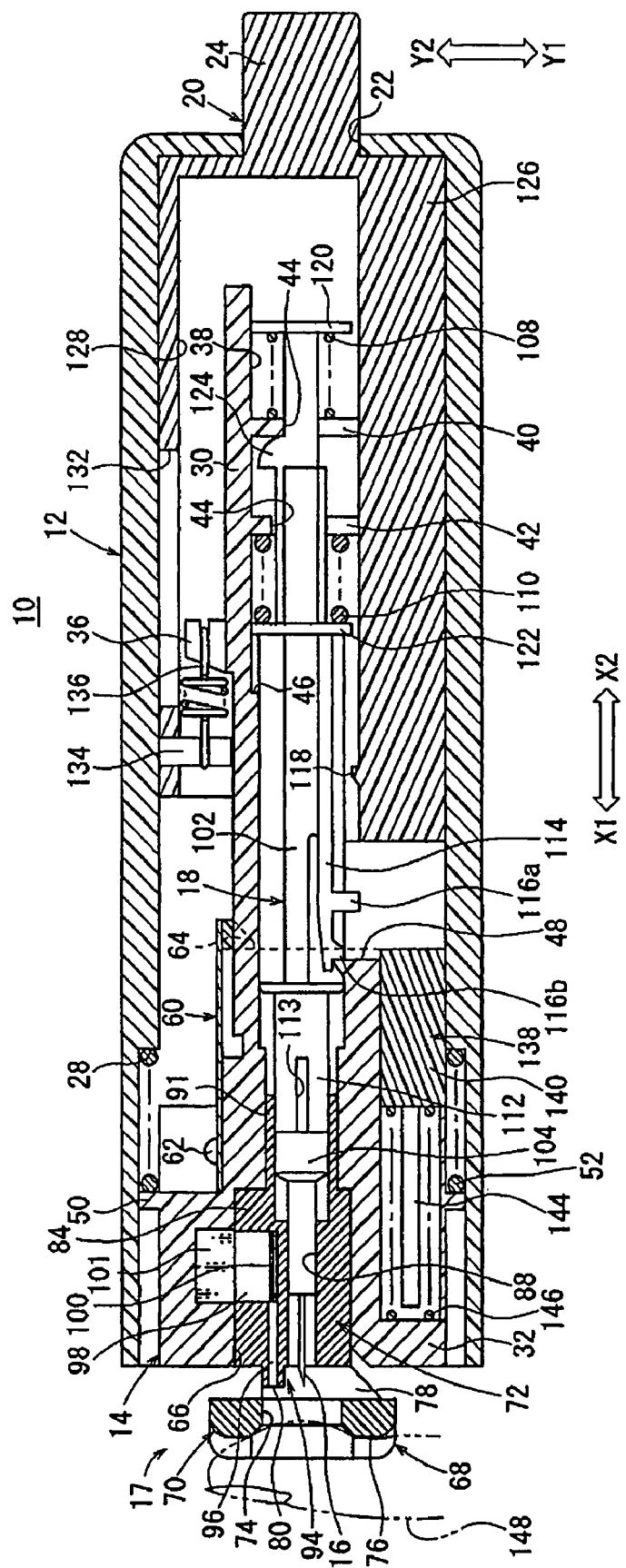
FIG. 4 is a longitudinal sectional view showing the condition where a contact mechanism of the blood component measurement device of FIG. 3 is pressed against the skin of a person to be measured.

The contact member 70 has a center hole (cavity) 74 through which a part of the puncturing unit 18 is passed, a depression 76 formed on one end side thereof and depressed in an arcuate shape corresponding to the shape of a fingertip 148 of the person to be measured (see FIG. 4), and a pair of slant parts 78 formed on the other end side and inclined at a predetermined angle (for example, 45°) relative to the axis of the contact member 70. Incidentally, the contact member 70 is formed in a tapered shape such that the diameter is gradually reduced from an end face, which comes into contact with the person to be measured, toward the center hole 74. Therefore, when the fingertip 148 is brought into contact with the contact member 70, any surface of the contact member 70 can be pressed appropriately, whereby outflow of blood upon puncturing can be accelerated.

The center hole 74 is formed at a substantially central part of the contact member 70, and is formed with such a diameter that the puncturing unit 18 and the introduction port 80 (described later) provided in the guide member 72 can be passed therethrough when the contact mechanism 68 is mounted to the holder 14.

The depression 76 is depressed in a concave shape so as to have substantially the same sectional shape along directions (directions of arrows Y1 and Y2) substantially orthogonal to the axis of the contact member 70. This ensures that when the person to be measured put his fingertip 148 into contact with the contact member 70, the fingertip 148 can be appropriately put into close contact with the contact member 70.

The pair of slant parts 78 are formed in such a direction (the direction of arrow X2) as to be spaced away from the depression 76, and are spaced from each other by a predetermined interval, with the center hole 74 as a center. The upper surfaces of the slant parts 78 are formed in a substantially flat surface shape substantially parallel to the axis of the contact member 70, and first slant surfaces 82 are formed which are inclined at a predetermined angle (for example, 45°) from end parts of the slant parts 78 toward the lower part side of the depression 76 (in the direction of arrow Y2). Incidentally, the pair of slant parts 78 are so disposed as to be substantially symmetric with each other, with the center hole 74 as a center.

In addition, pins (not shown) are mounted to mutually opposed side surfaces of the slant parts 78, and the pins are projected relative to the side surfaces and disposed at such positions as to be opposed to each other.

The guide member 72 includes a block part 84 formed in a substantially rectangular parallelepiped shape and fixed to the second mount hole 66 in the holder 14, a pair of guide parts 86 formed on both sides of the block part 84, and a holding hole 88 formed in a substantially central part of the block part 84 so as to hold a part of the puncturing unit 18. The guide parts 86 are provided with second slant surfaces 90 inclined at a predetermined angle relative to the axis of the guide member 72, and the inclination angle of the pair of second slant surfaces 90 is set to correspond to the inclination angle of the slant surfaces of the contact member 70. The guide parts 86 are so shaped as to be substantially symmetric, with the holding hole 88 as a center.

The block part 84 is provided with a mounted part 91 projected in a hollow cylindrical shape toward the puncturing unit 18 side (in the direction of arrow X2), and the mounted part 91 is held by being inserted into the first mount hole 38 in the holder 14.

In addition, the block part 84 is provided with guide holes 92 in side surfaces located on the guide part 86 sides, and the guide holes 92 are so inclined as to be substantially parallel to the inclination angle of the second slant surfaces 90. The block part 84 is disposed between the pair of slant parts 78 of the contact member 70, and the second slant surfaces 90 are put into contact with the first slant surfaces 82 of the contact member 70. The pins (not shown) of the contact member 70 are inserted in the guide holes 92, and the contact member 70 and the guide member 72 are engaged with each other through the guide parts 86 and the slant parts 78. This ensures that the contact member 70 can be displaced along the second slant surfaces 90 of the guide member 72 through the slant parts 78.

Specifically, the contact member 70 is slidingly displaceable in a direction (the direction of arrow A) inclined at a predetermined angle relative to the axis of the contact member 70. In this case, since the pins of the contact member 70 are inserted in the guide holes 92, the amount of displacement of the contact member 70 is restricted.

In addition, the block part 84 is provided with an introduction part (blood introduction part) 94 for introducing the blood flowing out from a person to be measured. The introduction part 94 has an introduction port 80 opened toward the exterior of the block part 84, a passage 96 which is connected to the introduction port and through which blood is circulated, and a circular recess 98 which communicates with the passage 96 and which is depressed by a predetermined depth from the upper surface of the block part 84.

Figure 5:
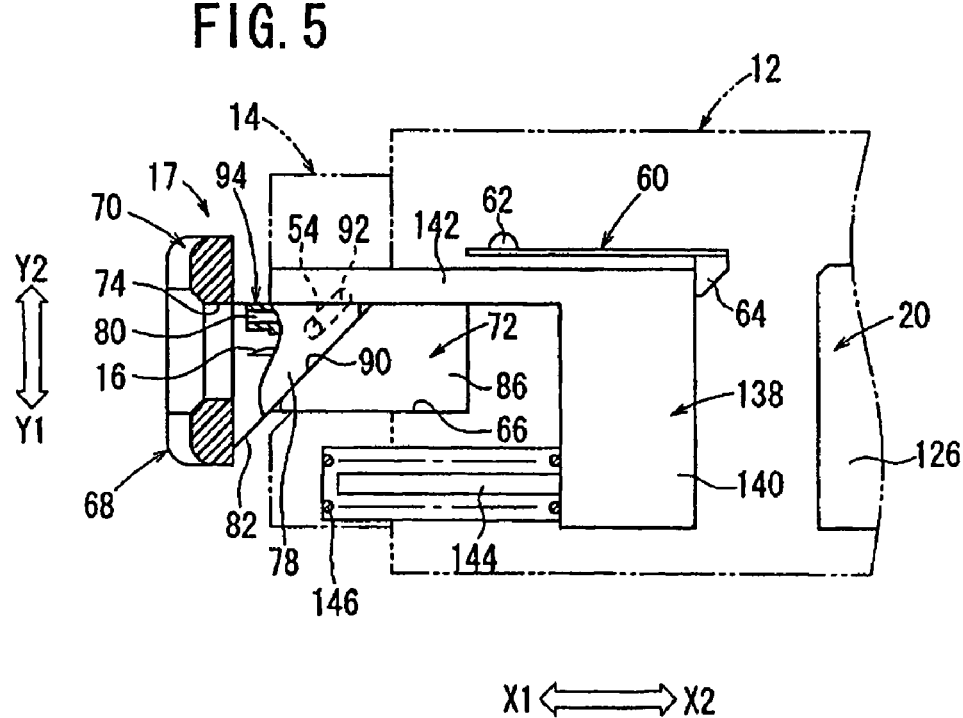
FIG. 5 is a schematic configuration view showing the positional relationships between a contact member and a guide member, in the contact mechanism of FIG. 4, and an introduction section and a puncturing unit.
Figure 6:
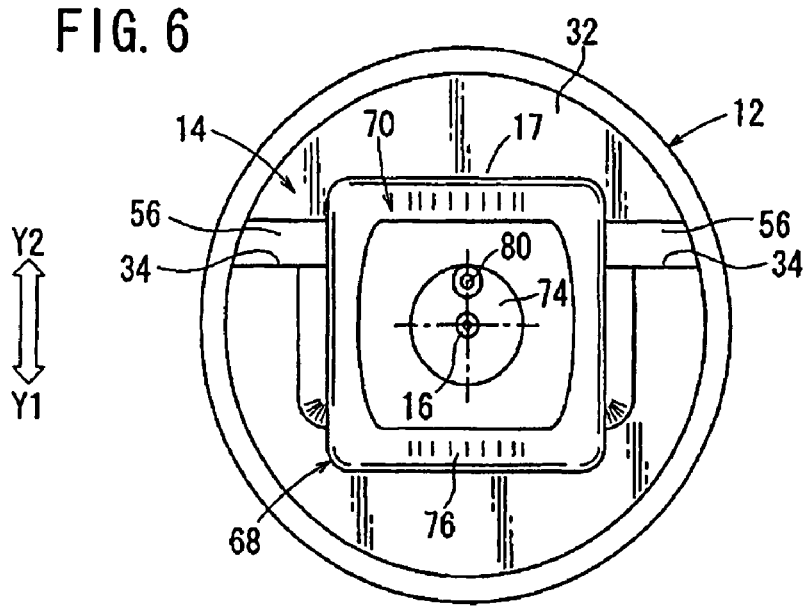
FIG. 6 is a front view of the blood component measurement device showing the condition where a puncture needle is located at the center of the contact member in the contact mechanism of FIGS. 4 and 5.

The introduction port 80 is projected by a predetermined length from an end face of the block part 84, and is disposed to be slightly spaced from the holding hole 88 in a direction substantially orthogonal to the axis of the holding hole 88 (see FIGS. 5 and 6).

The test paper 100 impregnated with a predetermined reagent is fixed in the circular recess 98. Examples of the material of the test paper 100 include polyether sulfone. Examples of the reagent include color formers such as glucose oxidase (GOD), peroxidase (POD), 4-aminoantipyrin, and N-ethyl N-(2-hydroxy-3-sulfopropyl). Besides, an electrochemical sensor can also be used as the measurement unit.

The blood introduced through the introduction port 80 is supplied to the test paper 100 impregnated with a predetermined reagent after circulating the circular recess 98 via the passage 96.

On the other hand, an optical measurement unit 101 including a light emitting device (for example, LED—Light Emitting Diode) and a photometric device (for example, PD—Photo Detector) is provided at such a position as to front on the second mount hole 66 and be opposed to the test paper 100, in the holder 14. An optical variation read through the optical measurement unit 101 is arithmetically operated by a control unit (not shown), and the result is displayed as a measurement result through a display unit.

The puncturing unit 18 includes a body section 102 formed to be long along the axial direction, a hub gripping section 112 which is formed at one end part of the body section 102 and which detachably holds the hub 104 of the tip for blood measurement 17, a return spring 108 which is interposed between the body section 102 and the first engagement wall 40 of the holder 14 and which biases the body section 102 toward the button unit 20 side (in the direction of arrow X2), and a puncturing spring 110 biasing the body section 102 in a direction (the direction of arrow X1) for spacing away from the button unit 20.

At one end part of the body section 102, the hub gripping section 112 having a plurality of slits 113 is formed to be expandable in the radial direction, and the reduced diameter section 105 of the hub 104 having the puncture needle 16 is held by being inserted in the hub gripping section 112. The hub gripping section 112 is displaceably held inside the mounted part 91 of the contact mechanism 68.

In addition, on one end side of the body section 102, a springy section 114 tiltable in a radial direction with a joint portion as a fulcrum is provided at the outer peripheral surface of the body section 102. The springy section 114 is normally biasing in a radial direction so as to space away from the outer peripheral surface. When the springy section 114 is depressed in a radial direction, it is tiltingly displaced toward the body section 102 side (in the direction of arrow Y2, in FIG. 3).

The springy section 114 is provided on its outer peripheral surface with a first projection 116a projecting in a radial direction, and the springy section 114 is depressed in a radial direction through the first projection 116a. The first projection 116a is disposed to be aligned with a projection 118 of the button unit 20 on substantially the same straight line along the axial direction.

Besides, the springy section 114 is provided at its tip part with a second projection 116b spaced from the first projection 116a by a predetermined interval, and the second projection 116b projects in a radial direction, like the first projection 116a. With the second projection 116b engaged with the second step part 48 of the holder 14, displacement of the puncturing unit 18 toward the hollow cylindrical section 32 side (in the direction of arrow X1) is restricted.

On the other hand, a first enlarged diameter part 120 enlarged in the radial direction is formed at the other end part of the body section 102, and a second enlarged diameter part 122 is formed at the substantially center along the axial direction of the body section 102. When the puncturing unit 18 is disposed inside the holder 14, the first enlarged diameter part 120 is disposed on the opposite side (the direction of arrow X2) of the hollow cylindrical section 32 with respect to the first engagement wall 40, and the second enlarged diameter part 122 is disposed on the hollow cylindrical section 32 side (the direction of arrow X1) relative to the second engagement wall 42.

The return spring 108 is interposed between the first enlarged diameter part 120 and the first engagement wall 40, to bias the puncturing unit 18 in a direction (the direction of arrow X2) for spacing away from the hollow cylindrical section 32 through the first engagement wall 40. In addition, the puncturing spring 110 is interposed between the second enlarged diameter part 122 and the second engagement wall 42, to bias the puncturing unit 18 toward the hollow cylindrical section 32 side (in the direction of arrow X1) through the second engagement wall 42.

A lock part 124 projecting in a radial direction is formed between the first enlarged diameter part 120 and the second enlarged diameter part 122, and an end face on the second enlarged diameter part 122 side (the direction of arrow X1) of the lock part 124 is formed in a substantially flat surface shape. More specifically, when the body section 102 is displaced toward the hollow cylindrical section 32 side (in the direction of arrow X1), the lock part 124 abuts on the second engagement wall 42, whereby displacement of the body section 102 along the axial direction is restricted (see FIG. 8).

The button unit 20 has a tubular section 126 formed in a hollow cylindrical shape, and a cylindrical button section 24 projecting from an end face of the tubular section 126. The button unit 20 is inserted to the other end side of the housing 12, and the button section 24 is inserted into the button hole 22 in the housing 12 so that it can be exposed to the exterior.

The tubular section 126 is provided therein with an insertion hole 128 in which the holder 14 and the puncturing unit 18 are inserted. The insertion hole 128 is provided, on its opened end side, with the projection 118 opposed to the springy section 114 of the puncturing unit 18. The projection 118 projects slightly from the inner wall surface of the insertion hole 128, and the opened end side of the insertion hole 128 is gradually inclined in a direction toward the button section 24 side (in the direction of arrow X2).

When the puncturing unit 18 is displaced along the insertion hole 128 toward the hollow cylindrical section 32 side (in the direction of arrow X1) and the projection 118 abuts on the first projection 116a of the springy section 114, the springy section 114 is depressed in a radial direction through the first projection 116a, whereby the outside diameter of the springy section 114 is reduced. As a result, the second projection 116b of the springy section 114 is separated away from the second step part 48, the puncturing unit 18 is unlocked, and the puncturing unit 18 becomes displaceable in a direction (the direction of arrow X1) for spacing away from the button unit 20.

In addition, the hollow cylindrical section 126 is provided in its outer peripheral surface with a window 132 opened by cutting out a substantially rectangular portion, whereby the inside and the outside of the hollow cylindrical section 126 are let communicate with each other. A spring pin 134 is mounted in the vicinity of the window 132, and, when the holder 14 is inserted in the button unit 20, a button spring 136 is interposed between the spring pin 134 and the projection 36 of the holder 14. In this case, the spring pin 134 is so disposed as to be located on the hollow cylindrical section 32 side (the direction of arrow X1) relative to the projection 36. Incidentally, the holder 14 is so inserted that its projection 36 is aligned with the spring pin 134 on substantially the same straight line.

The button spring 136 is included of a tension spring, and biases the spring pin 134 and the projection 36 toward each other, so that the button unit 20 and the holder 14 are displaced away from each other.

On the other hand, the stopper 138 is so disposed as to be located between the button unit 20 and the holder 14 when the button unit 20 is inserted in the inside of the housing 12.

The stopper 138 has an arcuate section 140 formed in a substantially C-shaped sectional shape, and a pair of bifurcated sections 142 are formed at both open end parts of the arcuate section 140. The main body section 30 of the holder 14 is inserted in the arcuate section 140, and the stopper 138 is displaceable along the holder 14 through the arcuate section 140.

In addition, the bifurcated sections 142 are formed to be substantially parallel to the axis of the arcuate section 140, and extend toward the hollow cylindrical section 32 side of the holder 14 (in the direction of arrow X1) with a substantially fixed width. Incidentally, the pair of bifurcated sections 142 are formed to have substantially the same shape.

When the main body section 30 of the holder 14 is inserted in the arcuate section 140, the bifurcated sections 142 are engaged with the guide grooves 34 of the holder 14. More in detail, the bifurcated sections 142 abut on the guide grooves 34, respectively.

This ensures that the stopper 138 is displaceable along the holder 14 under the guiding action of the guide grooves 34 through the pair of bifurcated sections 142. When the hook part 64 of the stopper hook 60 mounted to the holder 14 is engaged with an end face of the stopper 138, displacement of the stopper 138 toward the button unit 20 side (in the direction of arrow X2) is restricted.

In this case, the bifurcated sections 142 are inserted into the cutouts 56 in the holder 14, and abut on the upper surfaces of the slant parts 78 of the contact member 70 (see FIG. 5). In other words, since the bifurcated sections 142 are disposed on the upper side of the contact member 70, upward sliding displacement of the guide member 72 along the second slant surfaces 90 is restricted.

In addition, a guide shaft 144 substantially parallel to the bifurcated sections 142 is mounted to the substantially center of the arcuate section 140, and a stopper spring 146 is interposed between the stopper 138 and the hollow cylindrical section 32 of the holder 14 through the guide shaft 144. The stopper spring 146 is constantly biasing the stopper 138 in a direction (the direction of arrow X2) for spacing away from the hollow cylindrical section 32.

The blood component measurement device 10 and the tip for blood measurement 17 according to an embodiment of the present invention are configured basically as above-described, and their operations and effects will be described below.

First, the tip for blood measurement 7 is mounted to the second mount hole 66 of the holder through the guide member 72, and is pushed in toward the puncturing unit 18 side (in the direction of arrow X2). This ensures that the reduced diameter section 105 of the hub 104 held by the guide member 72 is inserted into the hub gripping section 112, and the hub 104 including the puncture needle 16 is held by the puncturing unit 18. As a result, preparation for blood measurement by the blood component measurement device 10 is completed. In this case, the test paper 100 is mounted in the circular recess 98 of the guide member 72, and the test paper 100 is opposed to the optical measurement unit 101 disposed in the holder 14.

Incidentally, the condition where the blood component measurement device 10 is not put in contact with the person to be subjected to blood sampling and measurement, the button section 24 is contained inside the housing 12 and the holder 14 is projected from one end of the housing 12 by a springy force of the coil spring 52 interposed inside the housing 12, as shown in FIG. 3, is taken as an initial condition in the following description.

Next, starting from the initial condition as shown in FIG. 3, for example, the person to be measured (not shown) grips the housing 12, and presses the contact mechanism 68 of the blood component measurement device 10 against his own skin (for example, the fingertip 148). By the pressure exerted on the skin side (in the direction of arrow X1) in the pressing of the contact mechanism 68, the holder 14 is displaced toward the housing 12 side (in the direction of arrow X2) against the springy force of the coil spring 52, and the end face of the holder 14 and the end face of the housing 12 become substantially flush with each other (see FIG. 4).

In addition, with the holder 14 displaced toward the housing 12 side (in the direction of arrow X2), the button section 24 of the button unit 20 is projected through the button hole 22 in the housing 12 to the exterior.

In this case, as shown in FIG. 5, upper parts of the slant parts 78 of the contact member 70 are covered with the bifurcated sections 142 of the stopper 138 passed through the cutouts 56. Therefore, sliding displacement of the contact member 70 along the guide member 72 is restricted, and the puncture needle 16 is held in the state of being disposed at the substantially center of the center hole 74 in the contact member 70 (see FIG. 6).

Figure 7:
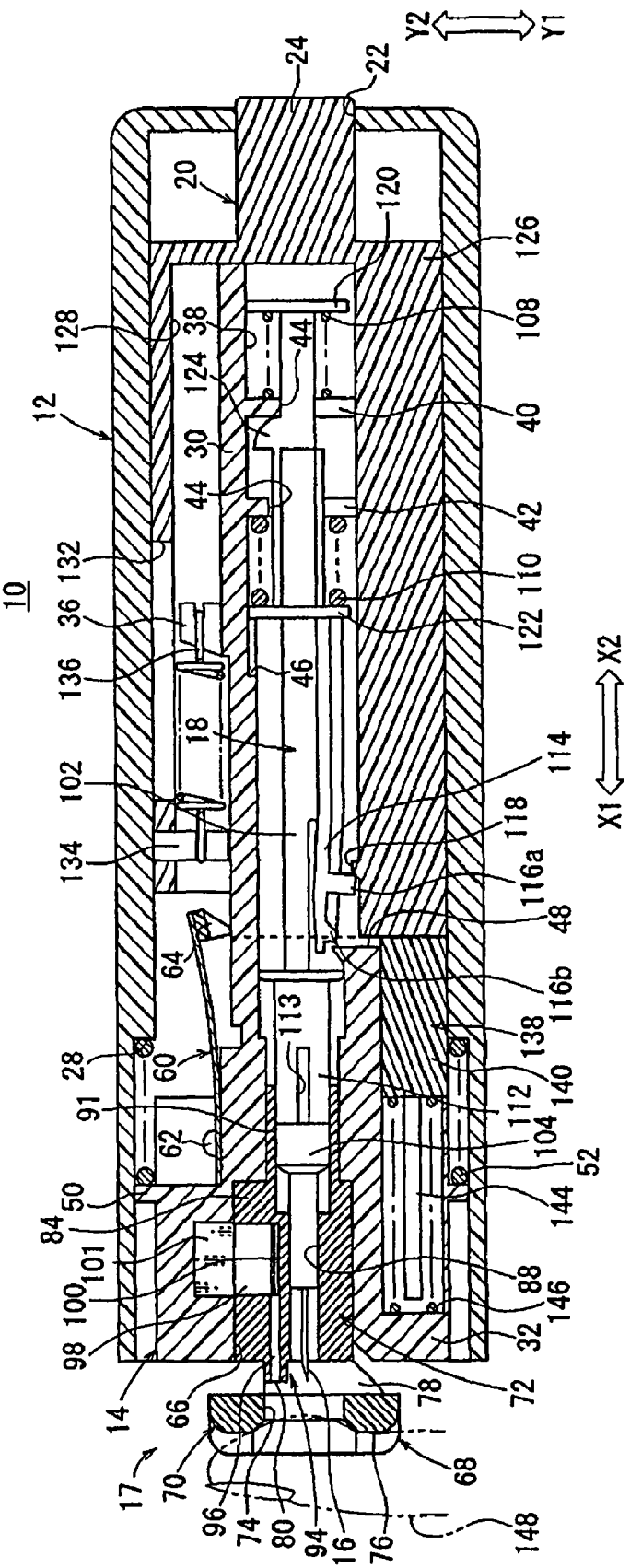
FIG. 7 is a longitudinal sectional view showing the condition where a button section in the blood component measurement device of FIG. 4 is pushed and the lock condition of the puncturing unit and a stopper is canceled.

Next, in the condition where the contact member 70 constituting the contact mechanism 68 is pressed against the fingertip 148 of the person to be measured, the button section 24 is pushed toward the housing 12 side (in the direction of arrow X1), whereby the button unit 20 is displaced toward the contact mechanism 68 side (in the direction of arrow X1) against the springy force of the button spring 136. Then, as shown in FIG. 7, the projection 118 of the button unit 20 pushes the first projection 116a of the puncturing unit 18 in a radially inward direction, to displace the springy section 114 toward the body section 102 side (in the direction of arrow Y2).

In this case, with the button unit 20 displaced toward the contact mechanism 68 side (in the direction of arrow X1), its tubular section 126 and an end face of the stopper 138 abut on each other. Therefore, the hook part of the stopper hook 60 having been engaged with the end face of the stopper 138 is upwardly pushed and tilted, to be separated from the end face of the stopper 138. As a result, the locked condition where displacement of the stopper 138 toward the button unit 20 side (in the direction of arrow X2) is restricted is canceled. Incidentally, the end face of the button unit 20 abuts on the stopper 138, and a pressure in the direction of arrow X1 is exerted on the stopper 138, so that the stopper 138 would not be displaced toward the button unit 20 side.

Figure 8:
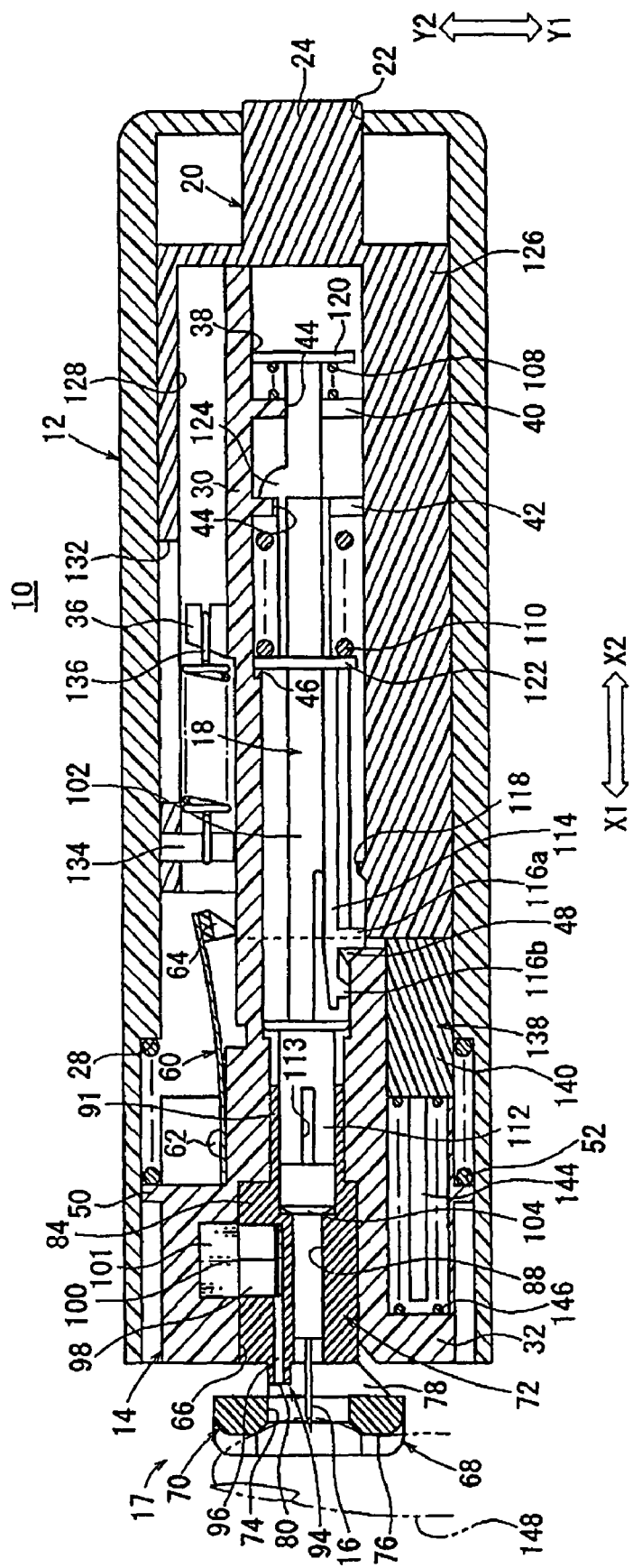
FIG. 8 is a longitudinal sectional view showing the condition where the puncture needle of the puncturing unit in the blood component measurement device of FIG. 7 has been displaced toward the side of the person to be measured, to puncture the skin of the person to be measured.

This ensures that the second projection 116b having been engaged with the second step part 48 of the holder 14 is disengaged, and the puncturing unit 18 is displaced toward the contact mechanism 68 side (in the direction of arrow X1) by the springy force of the puncturing spring 110 (see FIG. 8).

Then, the puncture needle 16 held at the tip of the puncturing unit 18 is pushed out through the center hole 74 in the contact member 70 to the outside relative to the center hole 74, to puncture the fingertip 148 of the person to be measured. This ensures that blood is let flow out from the punctured portion of the fingertip 148 which is punctured by the puncture needle 16. In this case, as shown in FIG. 8, the puncturing unit 18 is restricted in displacement along the axial direction because of the abutment of the lock part 124 on the second engagement wall 42, so that the amount of projection of the puncture needle 16 from the contact member 70 is restricted. In other words, the amount of puncture of the fingertip 148 by the puncture needle 16 is controlled to a predetermined amount.

Figure 9:
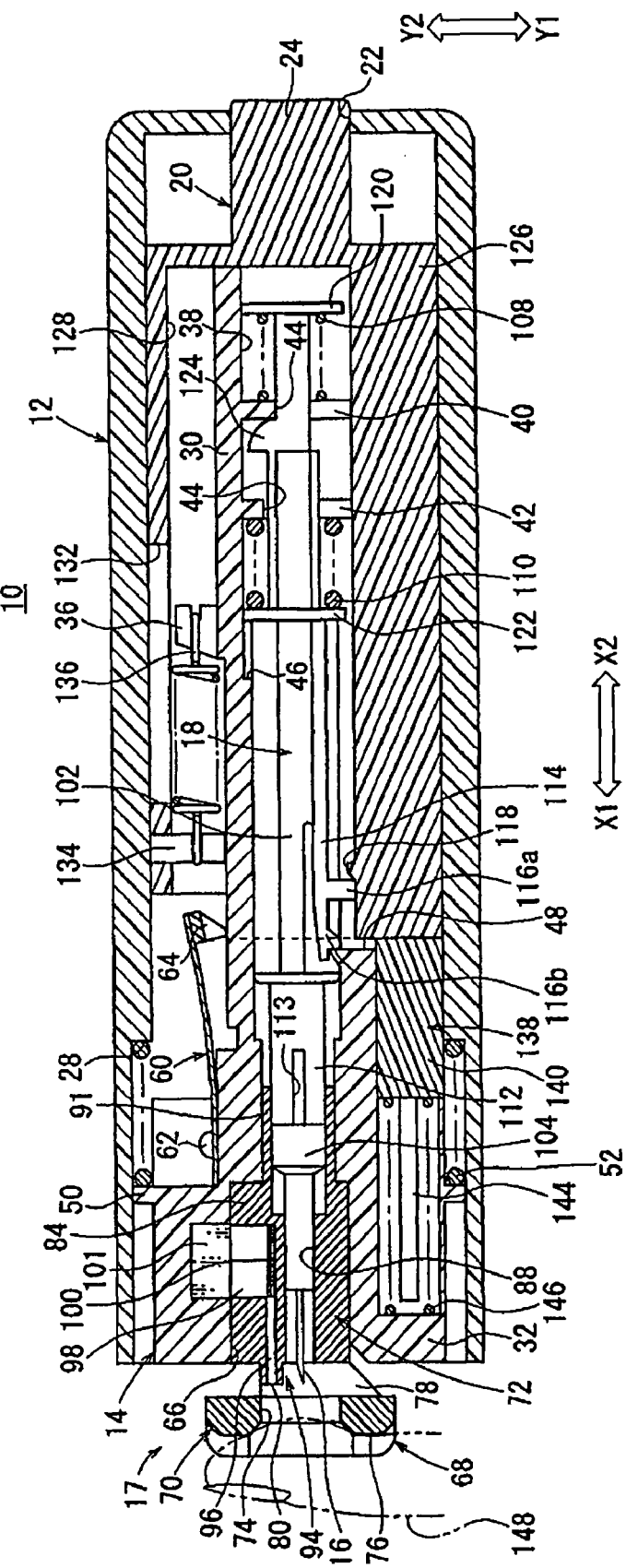
FIG. 9 is a longitudinal sectional view showing the condition where the puncture needle of the puncturing unit in the blood component measurement device of FIG. 8 has been pushed back by a springy force of a return spring after puncturing the skin.

Besides, the return spring 108 of the puncturing unit 18 is compressed in the direction of arrow X1 under the displacing action of the puncturing unit 18. Therefore, after the fingertip 148 is punctured by the puncturing unit 18, the puncturing unit 18 is immediately displaced in a direction (the direction of arrow X2) for spacing away from the fingertip 148 by the springy force of the return spring 108 (see FIG. 9). As a result, the puncturing unit 18 is returned to a position where the springy forces of the puncturing spring 110 and the return spring 108 balance, and is stopped there.

Figure 10:
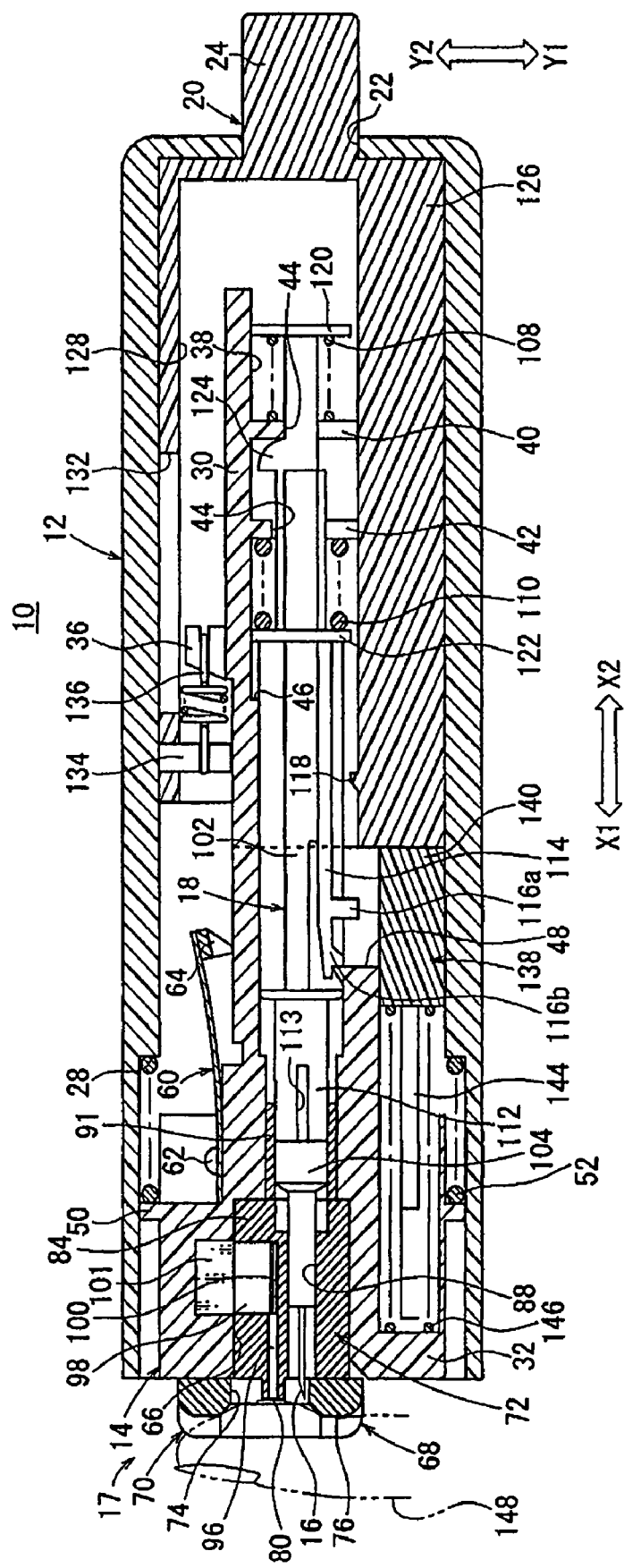
FIG. 10 is a longitudinal sectional view showing the condition where the stopper in the blood component measurement device of FIG. 9 has been displaced to the button unit side, the contact member has been slidingly displaced along a guide section, and the introduction section is located at the substantially center of the contact member.

Next, as shown in FIG. 10, the pressed condition of the button section 24 is canceled, whereby the button unit 20 is displaced in a direction (the direction of arrow X2) for spacing away from the holder 14 by the springy force of the button spring 136, and the button section 24 projects out through the button hole 22 to the exterior of the housing 12. Simultaneously, the stopper hook 60 is tilted upwards, with its one end fixed by the fixing screw 62 as a fulcrum, and, since the locking of the stopper 138 by the stopper hook 60 has been canceled, the stopper 138 is displaced toward the button unit 20 side (in the direction of arrow X2) by the springy force of the stopper spring 146. In other words, the stopper is displaced in the direction of arrow X2 as one body with the button unit 20 in the state of being in abutment on the end face of the button unit 20.

With the stopper 138 thus displaced, the contact member 70 having been locked by the bifurcated sections 142 of the stopper 138 becomes displaceable obliquely upwards (in the direction of arrow A). With the guide member 72 pushed toward the housing 12 side (in the direction of arrow X2), it is slidingly displaced obliquely upwards along the guide parts 86 of the guide member 72 (see FIG. 11). Incidentally, in this case, the fingertip 148 of the person to be measured which is being pressed against the contact member 70 is left as it is.

Figure 12:
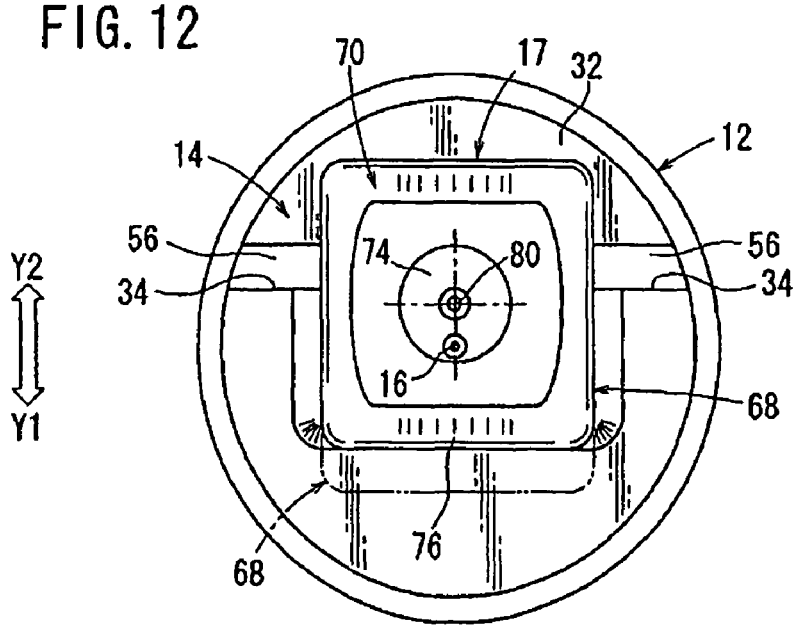
FIG. 12 is a front view of the blood component measurement device showing the condition where an introduction port of the introduction section is located at the center of the contact member in the contact mechanism of FIGS. 10 and 11.

This ensures that the contact member 70 is displaced slightly vertically upwards (in the direction of arrow Y2) relative to the holder 14 and toward the housing 12 side (in the direction of arrow X2) under the sliding action of the contact member 70, resulting in a shift from the condition where the puncture needle 16 of the puncturing unit 18 is inserted in the substantially center of the center hole 74 to the condition where the introduction port 80 is located at the substantially center of the center hole 74 (see FIG. 12). In other words, the amount of displacement in the vertical direction (the direction of arrow Y2 in the contact member 70 is substantially equal to the interval between the puncture needle 16 and the introduction port 80 along the vertical direction (the direction of arrows Y1, Y2).

Therefore, the introduction port 80 is brought to the position opposed to the punctured portion of the fingertip 148 of the person to be measured, and the blood left flow out from the punctured portion is adhered to the introduction port 80 and is thereby introduced into the passage 96. The blood is sucked up from the introduction port 80 into the passage 96 by capillarity, to be introduced to the test paper 100 mounted in the circular recess 98. Then, the blood 100 reacts with the reagent with which the test paper 100 is impregnated, and coloration according to the blood sugar level of the blood is obtained.

Finally, from the test paper 100 having undergone the coloration due to the blood sampled, a change in the amount of light received which is based on a change in color of the test paper 100 is optically read by the optical measurement unit 101, whereby the blood sugar level of the blood is measured. Then, the used tip for blood measurement composed of the contact mechanism 68 and the puncture needle 16 is discarded by a predetermined method.

Thus, in this embodiment, the puncture needle 16 in the puncturing unit 18 for puncturing the skin of a person to be measured and the introduction port 80 for introducing the blood flowing out from the punctured portion to the test paper 100 are disposed at a predetermined interval on a straight line, and the contact mechanism 68 coming into contact with the skin is slidingly displaceable in an oblique direction relative to the holder 14.

With the button section 24 depressed in the condition where the contact mechanism 68 is pressed against the person to be measured, the puncture needle 16 is pushed out through the center hole 74 in the contact member 70 toward the side of the person to be measured, and the puncture needle 16 located at the substantially center of the center hole 74 is let puncture the skin of the person to be measured. Thereafter, with the pressing of the button section 24 canceled, the unlocked contact member 70 is slidingly displaced in an oblique direction in the state of being pressed against the skin, resulting in the condition where the introduction port 80 is located substantially at the center of the center hole 74.

As a result, the punctured portion of the person to be measured where the blood is let flow out by the puncture needle 16 can be located opposite to the introduction port 80 through a sliding displacement together with the contact member 70.

Specifically, the contact member 70 can be shifted under the displacing action of the contact member 70 from the condition where the puncture needle 16 is located at the substantially center of the center hole 74 to the condition where the introduction port 80 is located at the substantially center of the center hole 74. This ensures that after the blood is let flow out by the puncture needle 16, the introduction port 80 can be moved to a position opposed to the punctured portion, and the blood can be efficiently introduced from the introduction port 80 to the test paper 100. In other words, the measurement in the blood component measurement device can be performed while using a minuter amount of blood.

Besides, for example, in the condition where the contact member 70 is slidingly displaced in the vertically upward direction (in the direction of arrow Y2) relative to the holder 14, the blood at the punctured portion is displaced while keeping the state of being substantially parallel to the end face of the introduction port 80 until it comes to such a position as to face the introduction port 80. In this case, the blood is let flow out in a convex shape in the manner of swelling from the surface of the skin at the punctured portion. Therefore, the blood may make contact with the portion surrounding the introduction port 80, and the blood may diffuse along the surface of the skin from the punctured portion.

On the other hand, in the blood component measurement device 10 according to the present invention, the contact member 70 is slidingly displaced in an oblique direction (the direction of arrow A) for spacing away from the person to be measured, relative to the holder 14 by which the guide member 72 is held; therefore, the blood at the punctured portion approaches the introduction port 80 gradually from an oblique direction. As a result, in the process of sliding displacement of the contact member 70, the blood swelling from the skin can be prevented from making contact with the introduction port 80.

Further, the person to be measured can press the blood component measurement device 10 against his own skin, and sliding displacement of the contact mechanism 68 can be effected by the pressing force. Therefore, the desired measurement can be performed easily by operating the blood component measurement device 10, and energy conservation can be contrived, as compared with the case of a blood component measurement device driven through an electrical signal or the like.

Incidentally, while the case where the contact mechanism 68 of the blood component measurement device 10 is pressed against the fingertip 148 of a person to be measured so as to puncture the fingertip 148 has been described in the embodiment above, the present invention is not limited to this, and the puncture needle 16 may be let puncture any portion of the skin of the person to be measured.

Besides, while the tip for blood measurement 17 according to this embodiment has a configuration in which the tip for blood measurement 17 has the puncture needle 16 and the test paper 100 constituting the measurement unit, the puncture needle 16 and the test paper 100 may be provided separately from the tip for blood measurement 17, or the contact mechanism 68 may be provided separately from the tip for blood measurement 17.

Figure 13:
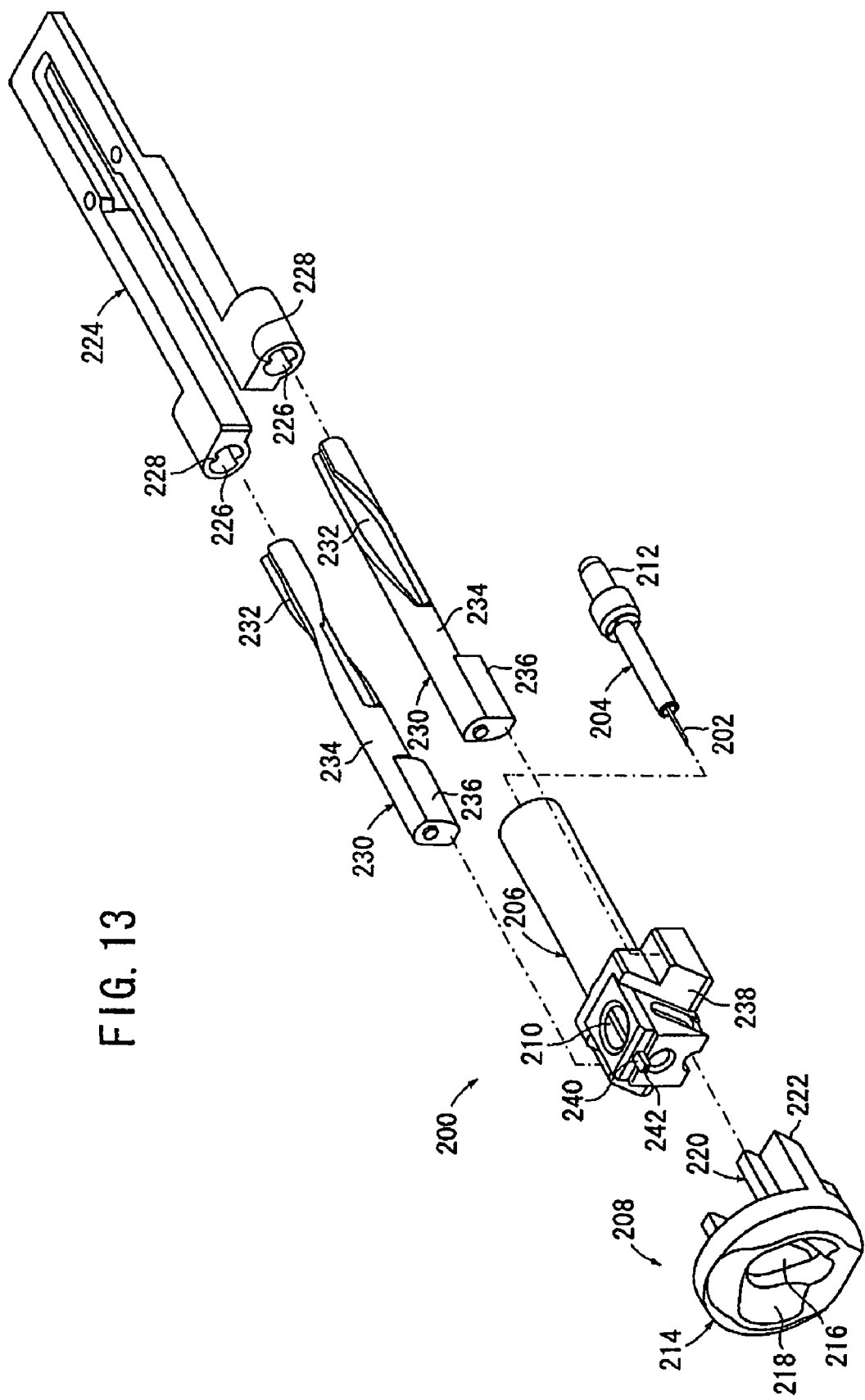
FIG. 13 is an exploded perspective view showing a tip for blood measurement according to a modified embodiment.

In addition, the tip for blood measurement 17 is not limited to the above-mentioned configuration; for example, a tip for blood measurement 200 configured as shown in FIG. 13 may also be used. Incidentally, the same components as those of the tip for blood measurement 17 according to the above-described embodiment will be denoted by the same reference symbols as used above, and detailed description of them will be omitted.

As shown in FIG. 13, the tip for blood measurement 200 includes a puncture needle 202, a hub 204 for holding the puncture needle 202, a tip body 206 for holding the puncture needle 202 and the hub 204 displaceably along the axial direction, a contact part 208 capable of coming into contact with the skin of a person to be measured, and a test paper 210 to which the blood of the person to be measured is to be introduced. Incidentally, FIG. 13 shows the tip for blood measurement 200 in an exploded perspective view for easy understanding.

The hub 204 is formed in a cylindrical shape, the puncture needle 202 is projected at one end of the hub 204, and a small diameter section 212 formed on the other end side is inserted into a hub gripping section 112 of a puncturing unit 18. As a result, the hub 204 is held relative to the hub gripping section 112 of the puncturing unit 18.

A contact section 208 is included of an annular contact member 214 coming into contact with a punctured portion of the skin of a person to be measured.

The contact member 214 includes a center hole 216 which is formed at the substantially center of the contact member 214 and through which the puncture needle 202 is to be passed, a depression 218 formed on one end side of the contact member 214 and depressed in an arcuate shape correspondingly to the shape of a fingertip of the person to be measured, and a pair of slant parts 220 which are formed on the other end side of the contact member 214 and which are inclined at a predetermined angle relative to the axis of the contact member 214.

The slant parts 220 are formed on both sides of the center hole 216, and first slant surfaces 222 are provided which are inclined to the lower side from end parts of the slant parts 220 toward the depression 218 side.

On the other hand, a slider 224 capable of sliding along the axial direction is provided inside the housing 12, and one-end parts of the slider 224 is enlarged in the width direction orthogonal to the axis of the slider 224. The enlarged width parts of the slider 224 are provided respectively with a pair of shaft holes 2261 penetrating the parts along the longitudinal direction of the slider 224. The shaft holes 226 are formed to be parallel to each other, and the inner peripheral surfaces of the shaft holes 226 are each provided with a pair of projected streak parts 228 along the axial direction. The projected streak parts 228 of each of the inner peripheral surfaces are provided to be opposed to each other.

Rotary shafts 230 are inserted in the shaft holes 226, and torsion grooves 232 formed in the outer peripheral surface of the rotary shaft 230 are engaged with the projected streak parts 228. The rotary shaft 230 includes a shaft part 234 to be inserted in the shaft hole 226, and a large-width presser part 236 which is formed at one end of the shaft part 234 and which is bulged in a radially outward direction relative to the shaft part 234. The torsion groove 232 is formed in the outer peripheral surface of the shaft part 234. The presser parts 236 are provided to be capable of abutment on the other end part of the contact member 214 constituting the tip for blood measurement 200, and upward displacement of the contact member 214 is restricted under their abutting action on the contact member 214. Specifically, the presser parts 236 of the rotary shafts 230 function as stoppers for restricting the displacement of the contact member 214.

The torsion grooves 232 are each so formed as to gradually turn by about 90° along the outer peripheral surface of the shaft part 234, with the axis of the shaft part 234 as a center. More specifically, the shapes of the torsion grooves 232 in the pair of rotary shafts 230 are so set as to be symmetrical with each other, with the axis of the slider 224 as a center.

When the slider 224 is displaced along the axial direction by another mechanism (not shown), the rotary shafts 230 are rotatingly displaced inside the shaft holes 226 by about 90° under the engaging actions between the projected streak parts 228 and the torsion grooves 232. In this case, the rotary shafts 230 are rotated in opposite directions so that the presser parts 236 are spaced away from each other. More specifically, the pair of presser parts 236 are brought into a substantially horizontal state through turning so as to approach the slots 26 in the housing 12. As a result, the condition where the displacement of the contact member 214 is restricted by the presser parts 236 is canceled, and the contact member 21 becomes capable of being displaced upward through the force of pressing against the skin of a person to be measured.

In the tip for blood measurement 200 configured as above, the pair of rotary shafts 230 in engagement with the projected streak parts 228 of the shaft holes 226 are rotated by about 90° in opposite directions attendantly on the displacement of the slider 224, resulting in cancellation of the condition where displacement of the contact member 214 is restricted by the presser parts 236. Attendant on this, the contact member 214 is displaced obliquely upwards along the second slant surfaces 238 of the tip body 206 by the force of pressing against the skin.

As a result, an introduction part 240 provided at an upper part of the tip body 206 is located to front on the center hole 216 in the contact member 214, and the introduction part 240 approaches a punctured portion of the skin of the person to be measured. Therefore, the blood let flow out from the punctured portion is sucked up into an introduction passage 242 by capillarity, is introduced to the test paper 210, and reacts with the reagent with which the test paper 210 is impregnated, whereby coloration according to the blood sugar level of the blood is obtained.

Furthermore, the blood component measurement device and the tip for blood measurement according to the present invention are not limited to the above-described embodiment, and various configurations can naturally be adopted within the scope of the gist of the invention.

The invention claimed is:

1. A blood component measurement device comprising:
a tip for blood measurement comprising a puncture needle possessing an axis and linearly movable for being advanced and retreated in an axial direction of the needle;
a contact section which has a cavity permitting said puncture needle to pass therethrough and which comes into contact with a skin, the contact section displaceable in a direction that is neither parallel nor perpendicular to the axis of said puncture needle;
a measurement unit for measuring a component of blood sampled; and
a blood introduction section spaced from said puncture needle in a direction substantially orthogonal to the axis of said puncture needle and communicating with said measurement unit, the blood introduction section being at a position out of contact with the skin when the puncture needle punctures the skin, and
after the skin is punctured by said puncture needle by linear advancement of the puncture needle in the axial direction, said blood introduction section is configured to be displaced from the position out of contact with the skin, in the axial direction of said puncture needle toward the skin and also in a direction substantially orthogonal to the axis of said puncture needle.

2. The blood component measurement device as set forth in claim 1,
wherein said blood component measurement device further includes a guide section holding said contact section, and
said blood introduction section is configured to be displaced under a guiding action of said guide section.

3. The blood component measurement device as set forth in claim 1,
wherein said contact section forms a part of said tip for blood measurement.

4. The blood component measurement device as set forth in claim 1,
wherein said blood introduction section forms a part of said tip for blood measurement.

5. The blood component measurement device as set forth in claim 1,
wherein said measurement unit forms a part of said tip for blood measurement.

6. The blood component measurement device as set forth in claim 1,
wherein said blood component measurement device includes a stopper which contacts the contact section for restricting displacement of said contact section, the stopper configured to move out of contact with the contact section after puncture of the skin by the puncture needle to permit the displacement of the contact section.

7. The blood component measurement device as set forth in claim 2,
wherein said contact section is provided with a first slant surface opposed to said guide section and inclined at a predetermined angle, said guide section is provided with a second slant surface making contact with said first slant surface, the first slant surface and the second slant surface are oriented at substantially the same angle, and said contact section is configured to be displaced relative to said guide section as a result of said first slant surface sliding along said second slant surface.

8. The blood component measurement device as set forth in claim 1,
wherein said blood component measurement device includes a housing, a button unit displaceably disposed inside said housing and operable to cancel a condition where the advancing and retreating of said puncture needle are restricted, and said button unit is exposed from said housing when said contact section is pressed against the skin.

9. The blood component measurement device as set forth in claim 1, wherein the blood introduction section is part of a guide section, and the guide section includes a sliding surface which is obliquely oriented relative to the axis of the needle, and wherein the blood introduction section is displaceable by sliding movement along the sliding surface.

10. A method for obtaining a blood sample comprising:

pressing a body part against a contact section which possesses a through hole;

linearly moving a needle possessing an axis in the axial direction of the needle through the through hole in the contact section to puncture skin of the body part at a puncture site with a tip end of the needle to result in a blood sample, the tip end of the needle being located in a first region of the through hole during puncture of the skin, the needle passing through a guide block during puncture of the skin, the guide block being movable relative to the contact section, the guide block including a blood introduction port connected to a passage, the blood introduction port being orthogonally spaced from the axis of the tip end of the needle and outside the first region;

relatively moving the guide block and the contact section after the puncture of the skin to cause the tip end of the needle to move away from said first region of the through hole of the contact section and to move the introduction port into the first region of the through hole of the contact section so that the introduction port is positioned adjacent the puncture site, wherein relatively moving the guide block and the contact section includes displacing the contact section in a direction that is neither parallel nor perpendicular to the axis of said puncture needle;

the blood sample at the puncture site being introduced into the introduction port and supplied to a test paper containing a reagent; and measuring a component in the blood sample supplied to the test paper.

11. The method according to claim 10, wherein the first region of the through hole of the contact section is a center of the through hole of the contact section.

12. The method according to claim 10, wherein the relatively moving of the guide block and the contact section comprises the guide block and the contact section sliding relative to one another in a direction oblique to the axis of the tip end of the needle.

* * * * *